United States Patent [19]

Hubert et al.

[11] 4,212,005

[45] Jul. 8, 1980

[54] MOVEMENT DETECTOR

[75] Inventors: Jacques Hubert, Saint-Avold; Jean-Marie Ory, Heillecourt, both of France

[73] Assignee: Societe Chimique des Charbonnages, Paris, France

[21] Appl. No.: 920,070

[22] Filed: Jun. 28, 1978

[30] Foreign Application Priority Data

Jun. 28, 1977 [FR] France ............................... 77 19869

[51] Int. Cl.² .......................... H04B 7/00; H04B 9/00
[52] U.S. Cl. ................................... 340/603; 73/304 C; 116/109; 361/284
[58] Field of Search ....................... 340/606, 605, 603; 325/182; 116/109, 112, 114 D, 114 H, 118 R, 118 A; 73/304 C; 361/284; 250/199

[56] References Cited

U.S. PATENT DOCUMENTS

| | | | |
|---|---|---|---|
| 2,768,368 | 10/1956 | Crane | 73/304 C |
| 2,771,592 | 11/1956 | Edmonson | 73/304 C |
| 4,122,718 | 10/1978 | Gustafson | 73/304 C |
| 4,133,453 | 1/1979 | Ohbora | 73/304 C |

*Primary Examiner*—David L. Stewart
*Attorney, Agent, or Firm*—Fitzpatrick, Cella, Harper & Scinto

[57] ABSTRACT

The invention relates to a movement detector, more particularly a sensor comprising a container partially filled with a liquid into which three electrodes extend. An input alternating signal is applied to two of the electrodes and an output signal amplitude modulated in accordance with movement of the liquid in the container, is detected from another two of the electrodes by means of a sensing circuit which includes a demodulator for detecting the amplitude modulation and a circuit arrangement which provides a container movement signal in response to successive peaks in the demodulated signal which are in excess of a given threshold value being spaced apart in time from one another by a time dependent upon the peak magnitudes of the demodulated signal.

15 Claims, 6 Drawing Figures

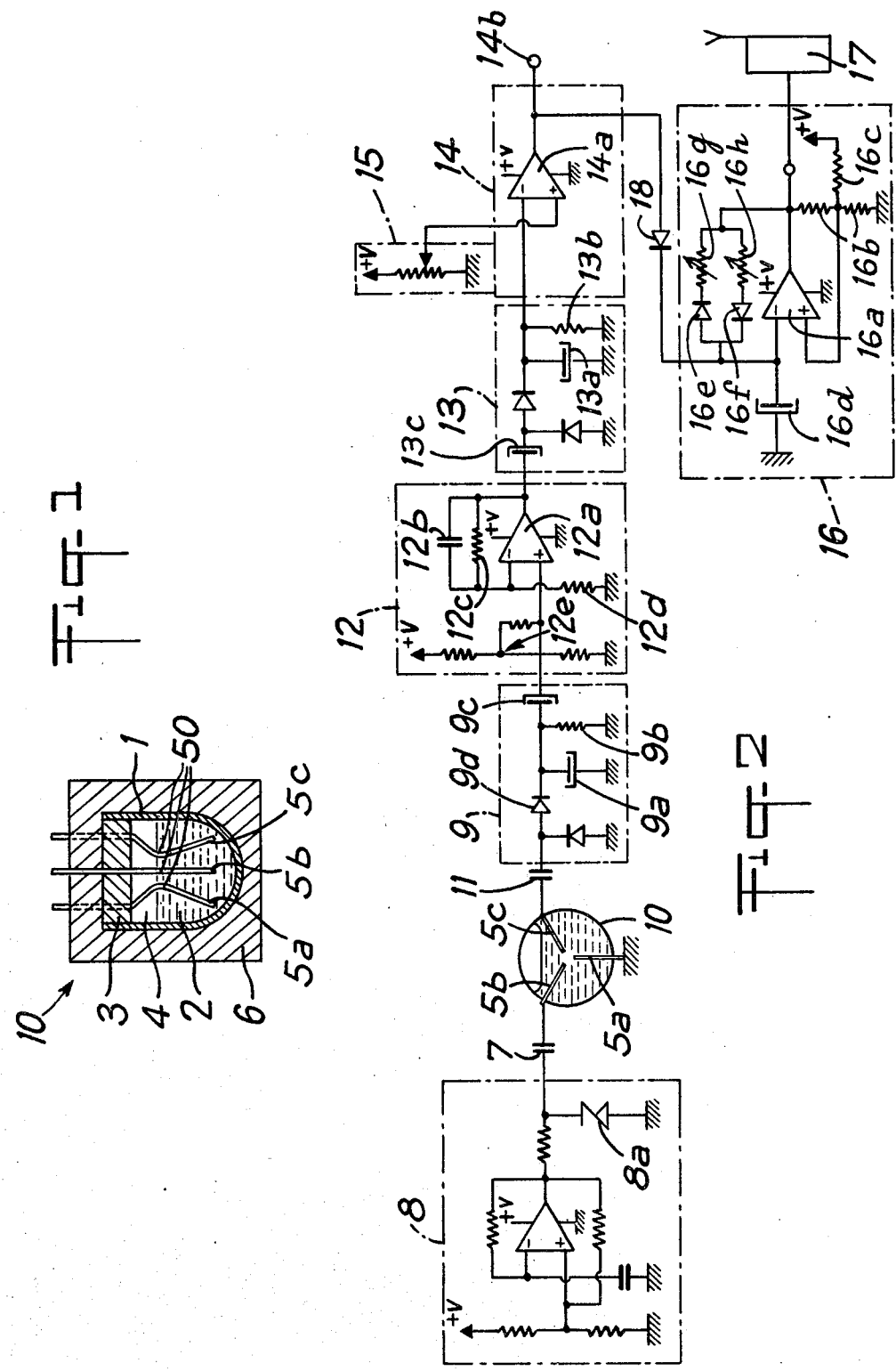

MOVEMENT DETECTOR

The present invention concerns a movement detector.

Movement detectors are known which include a sensor comprising a container closed in a fluid-tight manner partially filled with an electrically conductive liquid and three electrodes electrically insulated from one another and extending substantially within the container in such a manner as to be in contact with the liquid, a voltage generator connected between a first and a second electrode and a measuring circuit connected between the second and the third electrodes. Movement detectors of this type are known from the following prior publications: U.S. Pat. Nos. 3,042,888 and 3,164,023; an article by C. A. RATCLIFFE entitled "A Seismometer with a Water Wall as a Sensing Element" which appeared in the IEEE Transactions on geoscience electronics, vol. GE-10 No. 2, April 1972; German patent application (Federal Republic) DOS 2,332,124; and French Pat. No. 2,311,310.

It is an object of the present invention to provide an improved movement detector of this general type and from one aspect the invention provides a movement detector comprising a closed container partially filled with liquid, three electrodes extending into the liquid in such a manner as to always be in contact with the liquid whatever the orientation of the container may be, drive means adapted to apply to a first two of said electrodes an alternating input voltage, a sensing circuit responsive to an output voltage established across another two of said electrodes in response to said input voltage, said sensing circuit including a demodulator adapted to provide a demodulated signal indicative of the amplitude modulation of said output signal which modulation is caused by movement of the liquid in the container, means adapted to provide a container movement signal in response to successive peaks of the demodulated signal being of a magnitude greater than a predetermined threshold magnitude and occurring within a particular time range from one another, and said detector being only responsive to movement of the liquid occurring at a frequency within a particular range thereof.

The invention furthermore provides a movement detector comprising a container closed in a fluid tight manner and partially filled with a liquid, three electrodes electrically insulated from one another and extending within the container in such a manner as to be in contact with the liquid, drive means connected to a first and a second of said electrodes and arranged to apply an alternating voltage thereto, and a sensing circuit connected to said second and the third of the electrodes, wherein said drive means includes a source of d.c. voltage, an oscillator driven from said voltage and means for maintaining the peak amplitude of the alternating signal produced by the oscillator substantially constant notwithstanding fluctuations in said d.c. voltage, said electrodes extend into the container in such a manner as to be constantly in contact with the liquid whatever the orientation of the container may be, the viscosity of the liquid is so selected that the detector is only sensitive to movements of the container which have a frequency within a predetermined frequency range, capacitors are interposed between the drive means and the first electrode and between the sensing circuit and the third electrode to prevent a direct current passing through the liquid, said sensing circuit includes a demodulator for providing a demodulated signal indicative of movements of the liquid in the container, and said sensing circuit includes means adapted to provide a container movement signal in response to successive peaks in the signal from the demodulating means having an amplitude greater than a predetermined level and within a particular time range from one another.

A preferred embodiment of movement detector in accordance with the present invention has the following features and advantages, namely the drive means is adapted to produce an input alternating voltage at a frequency of at least ten times that of the movements it is desired to detect, the drive means being supplied from an independent source of d.c. voltage and being provided with means for maintaining the amplitude of the alternating signal which it provides, constant, whatever the fluctuations in the d.c. voltage provided by the source may be; the sensing circuit comprises a demodulation circuit in which the signal collected between the second and third electrodes is amplitude demodulated to form a demodulated signal varying continuously as a function of displacements and changes in orientation of the sensor; the container is compact in form and that each electrode extends substantially within the container in such a manner as to be constantly in contact with the liquid whatever the orientation of the sensor with respect to the vertical may be, so that the detector may function for any orientation of the container; the viscosity of the liquid is chosen so that the sensor is only sensitive to movements at frequencies included within a particular band of frequencies, termed a pass band; electrically isolating capacitive means are interposed between the drive means and the first electrode, so as to prevent a d.c. current from circulating in the liquid through the electrodes and from producing electrolysis which would release gas, which might cause the fluid-tight container to explode; the demodulated signal is processed in a circuit providing a signal which has an amplitude indicative of the peak to peak periodicity of the demodulated signal, which amplitude is compared in a comparator with a threshold value, the comparison information provided by the comparator determining the operation of a signalling device supplied from a separate source of d.c. voltage, by means of which the presence or absence of the emission of a signal by the signalling device may provide a remote indication of the presence or absence of movements of the sensor, the said movements having particular characteristics defined especially by the band pass of the sensor and by the threshold value.

The signalling device is constituted, for example, by a radio signal or an audio signal or a light source.

By virtue of this combination of characteristics, the preferred movement detector may be completely self-contained whilst being supplied from a cell or a battery; this detector may be mounted on any kind of member sensitive to the most varied movements since it functions in any position; by virtue of its independent signalling device, this detector provides remote indications of the presence or absence of movements with preselected characteristics. Furthermore, the sensor may be minaturized without losing its sensitivity nor its long life since the only element sensitive to movement which it comprises, is the liquid which it contains and the capacitive isolating means prevent electrolysis of the liquid by the electrodes.

By virtue of means permitting the peak value of the input signal to be maintained constant, it is possible to supply the drive means and to supply the signalling device from one and the same independent source of d.c. voltage such as a battery. The result is a still greater simplification and miniturisation of the detector.

A detector according to the invention can be used to selectively detect normal movements of a person; for this it is sufficient to adapt the detector so that it only detects movements, the frequency of which is between 0.1 and 20 Hz inclusive and preferably between 0.5 and 3 Hz. This filtering is obtained either by adjusting the viscosity of the liquid in the container and/or by using a band pass filter circuit.

Further features and advantages of the preferred embodiment of the invention will appear from the following description thereof given by way of illustrative example with reference to the accompanying drawings wherein:

FIG. 1 is a view in elevation and a diagrammatic vertical section through a sensor of a movement detector in accordance with the invention;

FIG. 2 is an electrical diagram of the detector, the sensor being shown diagrammatically in plan and in horizontal section;

Figure 3:
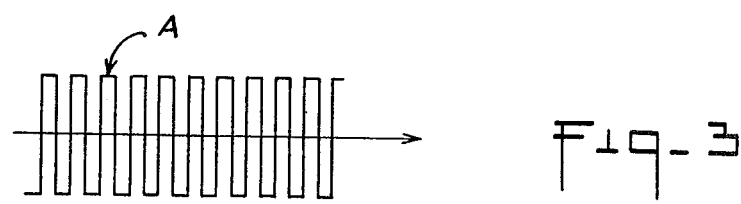
FIG. 3 is a waveform diagram showing the polarisation voltage generator signal, according to an embodiment of the invention.

The movement detector illustrated in the drawings comprises a sensor and an associated electronic circuit.

According to the embodiment illustrated in FIG. 1, the sensor 10 comprises a container 1 of electrically insulating material containing a liquid 2 slightly conductive to electricity. The container 1 has a compact shape and it is closed in a fluid-tight manner by a plug 3 and the liquid 2 does not completely fill the interior of the said container 1 so that a volume 4 filled with air, with a gas or empty, exists at the upper part of the said interior volume.

Three electrodes 5a to 5c passing through the plug 3 in a fluid-tight manner are immersed in the liquid 2; these electrodes are formed and disposed in the container 1 so that all three are constantly in contact with the liquid 2 whatever the inclination of the said container may be with respect to the vertical.

In the example illustrated in FIG. 1, each electrode 5a to 5c is bent at 50 in a central zone of its length and these electrodes are each disposed so that their bend 50 constitutes the point at which they are nearest to the other electrodes. The maximum level of the liquid 2 in the container 1 is arranged slightly above the bends 50 in the vertical position of the axis of the said container. Once closed by the plug 3, the container 1 is immersed in a block of resin 6 constituting a protection for the sensor against shock. Advantageously, this resin is of the epoxy type.

As the diagram of FIG. 2 shows, one of the electrodes 5a is connected to earth. A second electrode 5b is connected through an isolating capacitor 7 to a generator 8 of alternating voltage at high frequency, typically between some hundreds of Hertz and some tens of Kilo-Hertz inclusive. The generator 8 is supplied from an independent supply source (+V) and it comprises a zener diode 8a mounted in parallel with the output from the said generator 8. This diode ensures that the amplitude of the signal produced by the generator 8 remains constant whatever fluctuations there may be in the supply voltage +v from the source (+V). The capacitor 7, is of the non-electro-chemical type, that is to say a non-leakage type; the value of which is typically between 10 and 1000 nF inclusive, permits the prevention of a direct current causing the production of electrolysis effects in the sensor 10.

The alternating voltage taken from the third electrode 5c is demodulated in a circuit 9 which, in the illustrated example, is a diode pumping circuit, an isolating capacitor 11 also of the non-electro-chemical type, being interposed between the elements 5c and 9 for the purpose of preventing possible electrolysis effects within the sensor 10. The capacitors 7 and 11 must provide a very low impedance with respect to that of the sensor 10; advantageously, these capacitors are of the metallised film type, for example with a paper or plastics dielectric.

The variations in the output voltage from the circuit 9 are amplified by an amplifier circuit 12 and filtered by a band pass filter.

For these purposes, the circuit 12 comprises a differential amplifier 12a the positive input to which is connected to the output from the circuit 9; a capacitor 12b and a resistor 12c are connected in parallel between the negative input to the amplifier 12a and the output from the latter. A resistance bridge 12e, supplied by the voltage source (+V), ensures the correct polarity at the positive input to the amplifier 12a. The circuit 9 comprises a capacitor 9a and a resistor 9b mounted in parallel between earth and the cathode of the downstream diode 9d, as well as an output series capacitor 9c. The elements 12b and 12c provide a low-pass filter whilst the capacitor 9c in co-operation with the resistance bridge 12e of the circuit 12 provide a high-pass filter. The value of these components 12b, 12c, 9c and 12e are calculated so as to control the band width of the filter to frequency values corresponding to the type of movement which it is desired to detect by means of the sensor 10. A resistor 12d connecting the negative input to the amplifier 12a to earth, enables the gain of the amplifier circuit 12 to be determined.

The output signal from the circuit 12 is rectified in a circuit 13; then, the value of the signal produced by the circuit 13 is compared in a comparator circuit 14 with an adjustable reference voltage produced by a voltage divider 15 supplied by the source (+V). The comparator 14 comprises an operational amplifier 14a connected as an open loop amplifier and supplied by a source (+V). At its inverting input, the amplifier 14a receives the signal produced by the circuit 13. Thus, at its output 14b, it provides a zero voltage if the output voltage from the circuit 13 is higher than the reference voltage, and a constant voltage equal to the value +v of the independent voltage source (+V) appears at the output 14a if the output voltage from the circuit 13 is lower than the reference voltage.

Through the capacitor 7, the generator 8 applies to the electrode 5b, an alternating voltage signal of square waveform A, the diagram of which is represented in FIG. 3.

Figure 4:
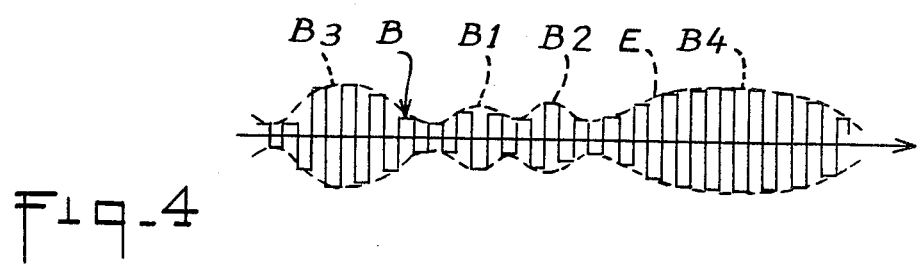
FIG. 4 is a diagram showing the corresponding modulated signal obtained between the second and third electrodes.

This voltage signal A is amplitude modulated by the movements of the liquid 2 within the sensor 10, such that a voltage signal B, which is represented by the waveform shown in FIG. 4, is applied to the electrode 5c.

Figure 5:
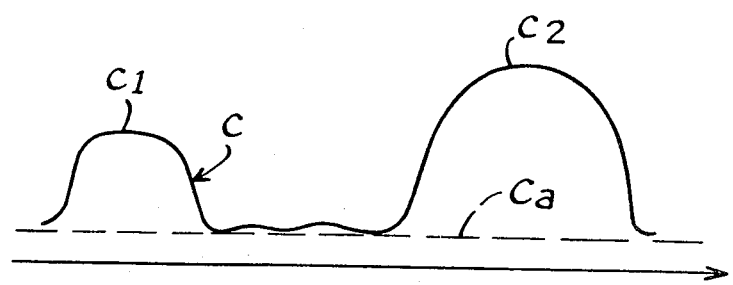
FIG. 5 is a diagram showing the corresponding signal demodulated and filtered.

The signal B is rectified and demodulated in the circuit 9 and this demodulated signal is filtered by the high-pass filter formed by the elements 9c and 12e described above. This signal is also filtered whilst being amplified by the amplifier 12a, 12b, 12c which acts as a low-pass filter only amplifying the components of the input signal, the frequency of which is lower than a cutoff frequency determined by the value of the components 12b and 12c. FIG. 5 illustrates the output signal C from the circuit 12. It can be seen that the components $B_1$ and $B_2$ of the envelope E of the modulated signal B have not been amplified at all, although the component $B_3$ and the component $B_4$, the sizes of which are clearly greater than those of the components $B_1$ and $B_2$, have been amplified considerably by the circuit 12.

The circuit 13 comprises a diode pumping circuit, the capacitor 13a of which is associated with a resistor 13b discharging the said capacitor to earth.

Figure 6:
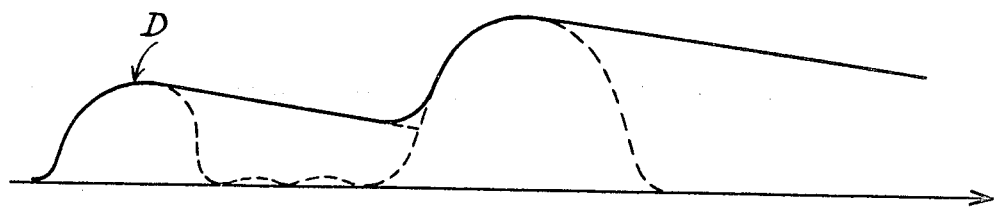
FIG. 6 is a diagram showing a signal measuring the crest to crest amplitude of the signal in FIG. 5, according to an embodiment of the invention.

A capacitor 13c is connected in series at the input to this diode pumping circuit. This capacitor 13c eliminates the minimum value Ca from the signal C. The circuit 13 is of similar design to a circuit providing at its output, a peak to peak measurement of an input voltage signal. However, the resistor 13b is chosen sufficiently low for the output signal D from the circuit 13, as represented in FIG. 6, to decrease substantially between the occurrence of two consecutive components $C_1$ and $C_2$ of the signal C. This rate of decrease is chosen at a value permitting initiation of the triggering action of the comparator at the end of the period of absence of the component of the signal C, a period of which the duration is longer the greater is the amplitude of the last detected component of the said signal C.

The circuit 16 is a relaxation oscillator with a cyclic ratio differing from "one"; to this end, it comprises an operational amplifier 16a to which are connected positive feedback resistors 16b, a resistor 16c connecting the positive input to the amplifier 16a to the source (+V). A capacitor 16d connects the negative input to the amplifier 16a to earth. Two diodes 16e and 16f are connected in parallel in opposite senses and in reverse feedback to the amplifier 16a and an adjustable resistor 16g and 16h is mounted in series with each of the diodes 16e and 16f respectively. This arrangement of the elements 16e to 16h enables an independent control of the duration of the high and of the duration of the low output signal from the circuit 16 to be effected (only being capable of receiving the values +v or zero volts)

When the output from the circuit 14 is at the high level as defined above, a current is injected through the diode 18 into the negating input to the amplifier 16a and, due to this, forces the circuit 16 to the low level, preventing it from oscillating.

Thus, when the liquid 2 is in motion, the alternating voltage collected by the third electrode 5c varies in amplitude, which gives rise to a signal after demodulation in the circuit 9 and amplification in the circuit 12; the latter circuit only amplifies those portions of the signal the frequency of which is to be found within a particular frequency band defined at the lower end by the cut-off frequency of the high-pass filter 9c, 12e and at the upper end by the cut-off frequency of the low-pass filter 12b, 12c.

The voltage of the signal is measured crest to crest in the circuit 13 and this measurement is compared in the circuit 14 with a reference the threshold of which can be regulated in accordance with the type of motion it is desired to detect. Thus the output of the comparator circuit 14 comprises a container movement signal indicative of movement of the liquid in the container, which occurs within a particular frequency range, the signal more particularly being indicative of whether successive peaks of the demodulated signal exceed a threshold level and lie within a particular time range from one another.

The resonant frequency of the sensor 10 depends on the dimensions of the container 1, 3; its attenuation depends on the viscosity of the liquid 2. Thus, it is possible to provide a sensor which responds to the needs of a paarticular application.

Thus, the sensor 10 is of the type providing a signal varying continuously as a function of the change in position of the container 1,3. The circuits 9 and 12 analyse the movements of the sensor 10 and only retain those which are provided at frequencies within the band pass defined above.

Thus, a signal is present at the output 14a from the circuit 14 when the sensor 10 is subject to movements satisfying determined characteristics of frequency and amplitude.

The output from the circuit 14 is connected to the control input to a cyclic generator 16 supplied from an independent source (+V), the generator periodically producing a pulse. These periodic pulses control the operation of a radio transmitter 17. These pulses are inhibited when the comparator 14 indicates an absence of movement. It has been noted that the essence of normal movements of a person gives rise to a signal TBF the frequency of which is between 0.1 and 20 Hz inclusive and preferably between 0.5 and 5 Hz so that, in the case where the detector is used for the supervision of persons by radio, the band pass of the apparatus is advantageously controlled to that frequency band by a suitable choice of components 9c, 12e, 12b and 12c.

The circuits 8, 12, 14 and 16 each make use of an operational amplifier.

These four operational amplifiers may be located in one and the same integrated circuit (for example a circuit known under the commercial name LM 324).

According to a non-limiting example, the liquid 2 which is used is a mixture of water and of ethanol containing a salt in solution such as copper sulphate in a ratio of 1/1000 by weight. The addition of a glucide such as glycerol, saccharose, etc., or of a similar substance enables the viscosity of the liquid to be increased as desired so as to widen the band pass of the sensor 10 whilst attenuating it. As a salt, copper sulphate—or another copper salt—is chosen in the case where the electrodes 5a, 5b and 5c are of copper because, in this case, an electrolysis does not produce liberation of gas risking causing explosion of the container 1,3.

Typically, the resistivity of the liquid 2 is between 1K and 100KΩ/cm inclusive, its viscosity is between $10^{-3}$ and 1000 poises inclusive and the volume of the interior of the container 1,3 is of the order of 0.1 to 200 cm3.

Apart from its application to the supervision of persons, the detector which has just been described may also be used to detect movements of the ground for example in seismology, soil mechanics, etc. It may also be used in anti-theft devices.

In the case of application to the supervision of a person, the detector is carried by the person and may thus detect the movements of the said person.

An anti-gel of some kind in solution in water, could be used instead of ethanol.

The radio transmitter 17 may be replaced by an audio signal generator such as a siren or by a luminous signal emitter such as an electric lamp.

We claim:

1. A movement detector comprising a sensor formed by a closed container partially filled with liquid, at least two electrodes electrically insulated from each other and in contact with said liquid, measuring means connected with said electrodes and providing a measuring signal whose amplitude is a function of the impedance between said electrodes, a detection circuit responsive to said measuring signal for measuring the amplitude of the variations of said measuring signal, and a threshold circuit responsive to said detection circuit for supplying an informative signal whenever said amplitude of variation becomes smaller than a predetermined threshold.

2. A movement detector in accordance with claim 1 including filtering means arranged to pass preferentially frequency components of the measuring signal which lie within a predetermined range.

3. A movement detector in accordance with claim 2 wherein said drive means comprises a source of d.c. supply voltage, an oscillator arranged to produce said alternating voltage in response to said supply voltage, and a blocking capacitor connected between the output of the oscillator and one of said first two of said electrodes, said blocking capacitors being arranged to prevent the passage of direct current to the liquid.

4. A movement detector in accordance with claim 3 wherein said demodulator includes a diode pump circuit.

5. A movement detector in accordance with claim 4 including a high-pass filter comprising a capacitor and a resistor connected to the output of the diode pump circuit, an operational amplifier connected to the output of the high-pass filter, and a feedback loop for the amplifier, said feedback loop including a resistor and a capacitor to define a low-pass filter.

6. A movement detector in accordance with claim 5 wherein said container movement signal providing means comprises a diode pump circuit connected to the output of the amplifier and arranged to charge a capacitor in response to the peaks of the signal produced by the amplifier, a resistor arranged to discharge the capacitor between said peaks, means for establishing a predetermined d.c. voltage level, and a comparator arranged to compare the voltage developed across said capacitor with said predetermined voltage level.

7. In a movement detector comprising a container closed in a fluid tight manner and partially filled with a liquid, three electrodes electrically insulated from one another and extending within the container in such a manner as to be in contact with the liquid, drive means connected to a first and a second of said electrodes and arranged to apply an alternating voltage thereto, and a sensing circuit connected to said second and the third of the electrodes the improvement comprising that said drive means includes a source of d.c. voltage, an oscillator driven from said voltage and means for maintaining the peak amplitude of the alternating signal produced by the oscillator substantially constant notwithstanding fluctuations in said d.c. voltage, said electrodes extend into the container in such a manner as to be constantly in contact with the liquid whatever the orientation of the container may be, the viscosity of the liquid being selected so that the detector is only sensitive to movements of the container which have a frequency within a predetermined frequency range, capacitors respectively interposed between the drive means and the first electrode and between the sensing circuit and the third electrode to prevent a direct current passing through the liquid, said sensing circuit including a demodulator for providing a demodulated signal indicative of movements of the liquid in the container, and said sensing circuit including means adapted to provide a container movement signal in response to successive peaks in the signal from the demodulating means having an amplitude greater than a predetermined level and within a particular time range from one another.

8. A movement detector in accordance with claim 7 wherein said electrodes are bent towards one another in central regions thereof.

9. A movement detector in accordance with claim 7 wherein said liquid comprises a mixture of water and an anti-gel, the mixture containing a salt in solution.

10. A movement detector in accordance with claim 7 including an oscillator adapted to provide an oscillatory signal in response to said container movement signal, and a signalling device adapted to transmit a signal in response to the oscillatory signal from the oscillator.

11. A movement detector in accordance with claim 10 wherein the signalling device comprises a radio transmitter.

12. A movement detector in accordance with claim 10 wherein the signalling device comprises a light source.

13. A movement detector in accordance with claim 7 wherein the sensing circuit includes a filtering means arranged to pass preferentially frequency components of the demodulated signal lying within a particular frequency band.

14. A movement detector in accordance with claim 13 wherein the band pass of said filtering means is between 0.1 and 20 Hz inclusive.

15. A movement detector in accordance with claim 14 wherein the band pass of said filtering means is between 0.5 and 3 Hz.

* * * * *